(12) United States Patent
Sukovic et al.

(10) Patent No.: US 7,397,890 B2
(45) Date of Patent: Jul. 8, 2008

(54) CT SYSTEM WITH SYNTHETIC VIEW GENERATION

(75) Inventors: Predrag Sukovic, Birmingham, MI (US); Neal Clinthorne, Ann Arbor, MI (US); Joseph Webster Stayman, Ann Arbor, MI (US); Miodrag Rakic, Redondo Beach, CA (US)

(73) Assignee: Xoran Technologies, Inc., Ann Arbor, MI (US)

( * ) Notice: Subject to any disclaimer, the term of this patent is extended or adjusted under 35 U.S.C. 154(b) by 0 days.

(21) Appl. No.: 11/410,526

(22) Filed: Apr. 25, 2006

(65) Prior Publication Data

US 2006/0239400 A1    Oct. 26, 2006

Related U.S. Application Data

(60) Provisional application No. 60/674,638, filed on Apr. 25, 2005, provisional application No. 60/771,797, filed on Feb. 9, 2006.

(51) Int. Cl.
*A61B 6/14* (2006.01)
(52) U.S. Cl. .............................. 378/38; 378/4
(58) Field of Classification Search ............. 378/38–40, 378/4, 168, 190–191
See application file for complete search history.

(56) References Cited

U.S. PATENT DOCUMENTS

| | | | |
|---|---|---|---|
| 5,058,147 A | 10/1991 | Nishikawa et al. | |
| 5,278,756 A * | 1/1994 | Lemchen et al. | 600/587 |
| 5,901,199 A * | 5/1999 | Murphy et al. | 378/65 |
| 6,064,391 A * | 5/2000 | Sano et al. | 345/424 |
| 6,068,482 A | 5/2000 | Snow | |
| 6,081,739 A | 6/2000 | Lemchen | |
| 6,493,415 B1 * | 12/2002 | Arai et al. | 378/4 |
| 6,845,175 B2 | 1/2005 | Kopelman et al. | |
| 7,154,985 B2 | 12/2006 | Dobbs et al. | |

(Continued)

OTHER PUBLICATIONS

Rohlfing et al., Progressive Attenuation Fields: Fast 2D-3D Image Registration Without Precomputation, C. Barillot, D.R. Haynor, and P. Hellier, LNCS 3216, pp. 631-638.*

(Continued)

*Primary Examiner*—Courtney Thomas
*Assistant Examiner*—Alexander H Taningco
(74) *Attorney, Agent, or Firm*—Carlson, Gaskey & Olds

(57) ABSTRACT

A CT scanner system provides projection-like images of a patient volume. After a CT scan is obtained and a three-dimensional model of the patient is created, any synthetic view can be generated by choosing any array of projection lines, e.g. between a point and a surface (a flat plane, curved plane, spherical, etc) or between two surfaces (parallel or not) and summing across the projection lines. The synthetic projections can mimic certain traditional views, such as a ceph scan, Water's view, Caldwell's projection, etc or can provide a new view that is impossible or impractical with traditional x-ray equipment, such as a perfect parallel projection, or a projection that does not pass all the way through the patient.

4 Claims, 5 Drawing Sheets

U.S. PATENT DOCUMENTS

| | | | |
|---|---|---|---|
| 2001/0036303 A1* | 11/2001 | Maurincomme et al. | 382/132 |
| 2004/0066877 A1* | 4/2004 | Arai et al. | 378/4 |
| 2004/0197727 A1* | 10/2004 | Sachdeva et al. | 433/24 |
| 2005/0047638 A1 | 3/2005 | Suzuki et al. | |
| 2005/0242380 A1 | 11/2005 | Suzuki et al. | |
| 2006/0153434 A1* | 7/2006 | Wang | 382/128 |
| 2007/0030950 A1 | 2/2007 | Sa et al. | |
| 2007/0030951 A1 | 2/2007 | Park et al. | |
| 2007/0030952 A1 | 2/2007 | Sa et al. | |
| 2007/0086559 A1 | 4/2007 | Dobbs et al. | |

OTHER PUBLICATIONS

Penney et al., A Comparison of Similarity Measures for Use in 2-D-3-D Medical Image Registraion, IEEE Transaction on Medical Imaging, vol. 17, No. 4, Aug. 1998.*

Lemieux et al., A Patient-to-computed-tomography Image Registration Method Based on Digitally Reconstructed Radiographs, Med Phys, vol. 21, No. 11, Nov. 1994.*

Wein et al., Intensity Based Rigid 2D-3D Registration Algorithms for Radiation Therapy, paper submitted at Technische University, Dec. 15, 2003.*

* cited by examiner

CT SYSTEM WITH SYNTHETIC VIEW GENERATION

This application claims priority to U.S. Provisional Application Ser. Nos. 60/674,638, filed Apr. 25, 2005 and 60/771,797, filed Feb. 9, 2006.

BACKGROUND OF THE INVENTION

The present invention relates to a CT scanner system.

There are many types of specialized x-ray equipment or arrangements each dedicated to providing a specific view or type of x-ray projection. For example, such as panoramic dental x-rays, Water's view x-rays, Caldwell's projection, and cephalometric x-rays are each typically provided by a different type of x-ray machine or arrangement. Each of these devices occupies space, possibly even a dedicated room.

The cephalometric x-ray (or "ceph scan") equipment in particular occupies a large space. Maxillofacial surgeons, orthodontists and other doctors use cephalometrics to diagnose, plan and predict maxillofacial surgeries, orthodontic treatment and other treatments that could affect the shape and appearance of the face. One important part of the cephalometric analysis is starting with a ceph scan of the patient's head. Primarily, lateral x-ray ceph images are taken of the patient, although other images can be used in addition.

In order to obtain an accurate lateral x-ray ceph image, a parallel projection from the x-ray source to the x-ray detector or film is desired. Otherwise, the distortion from incident angles of the x-rays will distort the ceph image. To obtain a sufficiently parallel projection, the x-ray source is placed at a relatively great distance (5 to 10 ft) from the patient. Therefore, the room dedicated to performing this type of x-ray must be large.

SUMMARY OF THE INVENTION

The present invention provides a CT scanner system that can provide projection-like images of a patient volume.

For purposes of illustration, an example embodiment of a CT scanner system that can provide a choice of a plurality of "synthetic" projection-like images will be described; however, a single CT scanner dedicated to providing a single type of projection-like images is also within the scope of the present invention.

In general, after a CT scan is obtained and a three-dimensional model of the patient is created, any synthetic view can be generated by choosing any array of projection lines, e.g. between a point and a surface (a flat plane, curved plane, spherical, etc) or between two surfaces (parallel or not) and summing across the projection lines. The synthetic projections can mimic certain traditional views, such as a ceph scan, Water's view, Caldwell's projection, etc or can provide a new view that is impossible or impractical with traditional x-ray equipment, such as a perfect parallel projection, or a projection that does not pass all the way through the patient.

Because of the inherent noise reduction in the synthetic projection process, a very low dose CT scan can be used. The CT scan itself would be considered to be well below what is considered diagnostic quality as a CT scan, but produces a synthetic projection that is very good diagnostic quality. Additionally, dosage can be further reduced by varying the dosage of certain images and/or by varying the angular spacing between certain images during the acquisition of the CT scan.

A user interface may be provided for choosing among a plurality of synthetic views. If the user chooses which synthetic views may be desirable from the user interface before the CT scan is performed, the CT scan can be optimized to provide sufficient information for each desired synthetic view while minimizing x-ray dose. Alternatively, the CT scan can always be performed such that any of the available options for synthetic views will be available afterwards.

After the CT scan (whether or not optimized for a subset of available synthetic views), a user interface displays the available synthetic views to the user, e.g. buttons for each of "Ceph," "Waters," "Compare Halves," etc. For example, by clicking a button for "Ceph," a synthetic ceph scan is displayed.

When the projection is selected (either a pre-defined projection, or a projection defined more specifically by the user), the CT scanner system then creates the synthetic projection by defining the array of projection lines, e.g. between a point and a surface (a flat plane, curved plane, spherical, etc) or between two surfaces (parallel or not) and summing across the projection lines. The resultant two dimensional synthetic projection is then displayed. The user interface may also provide the user with the option of creating a custom projection, such as by drawing the point and the surface or by drawing two surfaces, or otherwise specifying the projection lines.

BRIEF DESCRIPTION OF THE DRAWINGS

Advantages of the present invention can be understood by reference to the following detailed description when considered in connection with the accompanying drawings wherein.

DETAILED DESCRIPTION OF THE PREFERRED EMBODIMENTS

Figure 1:
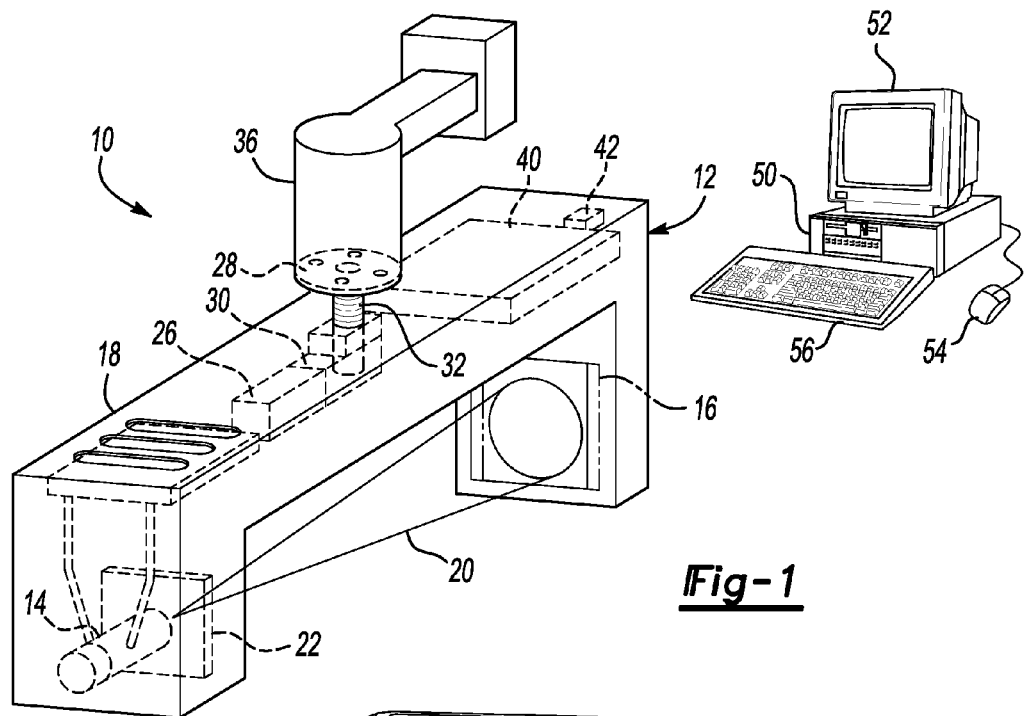
FIG. 1 illustrates one embodiment of the scanning system of the present invention.

One possible embodiment of a scanning system 10 according to the present invention is shown in FIG. 1. The scanning system 10 includes CT scanner 12 having an x-ray source 14 and x-ray detector 16 mounted opposite one another on a gantry 18. Suitable CT scanners 12 are known, but would preferably utilize a cone-beam x-ray source 14 and a flat-panel detector 16. The detector 16 has a converter for converting x-rays 20 from the x-ray source 14 to visible light and an array of photodetectors behind the converter. A collimator 22 may be mounted in the gantry 18 in front of the x-ray source 14.

A first motor 26 is mounted in the gantry 18 for rotating the gantry 18 relative to a mounting plate 28. The first motor 26 may directly drive the mounting plate 28, or a gear box may be provided between the first motor 26 and mounting plate 28. The mounting plate 28 may be mounted to an arm 36 supported above the floor. A second motor 30 may be provided to selectively move the gantry 18 vertically relative to the mounting plate 28. The first and second motors 26, 30 may move the gantry 18 rotatably and vertically, respectively, relative to a shaft 32 extending from the arm 36.

An optional on-board computer 40 may provide some local storage and/or processing of images from the detector 16 for subsequent transmission via a transmitter 42 to a main computer 50. The main computer 50 includes a display 52 and input devices, such as a mouse 54 and keyboard 56. The images may alternatively be transmitted via wires or cables (not shown) to the main computer 50 for processing and display. The computer 50 includes at least one processor, memory and/or other storage and includes computer readable media storing computer programs to perform the functions described herein. Any CT scanner 12 could be utilized in the present invention, as the present invention is independent of the specific imaging technology utilized.

Figure 2:
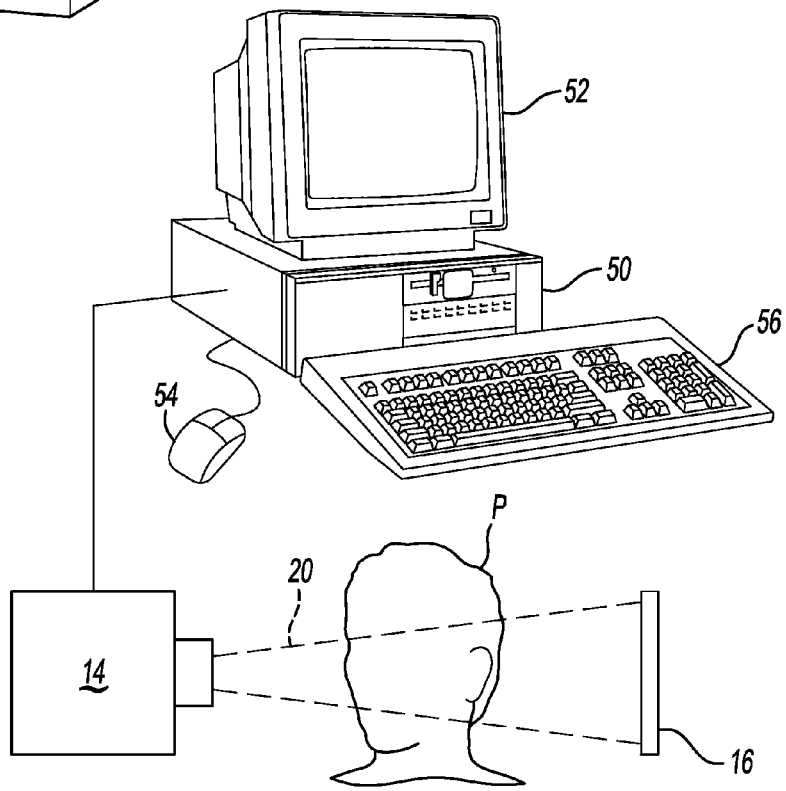
FIG. 2 illustrates the scanning system of FIG. 1 in use scanning a patient.

Referring to FIG. 2, in operation, the patient (or more specifically in this example, the patient's head, although other parts of the patient could also be scanned) P is positioned between the source 14 and detector 16. The first motor 26 rotatably drives the gantry 18 at least partially about the patient P, while the detector 16 takes a plurality of x-ray images of the patient P at a plurality of rotational positions. A three-dimensional CT image is then reconstructed from the plurality of x-ray images utilizing any known techniques and algorithms.

Figure 2A:
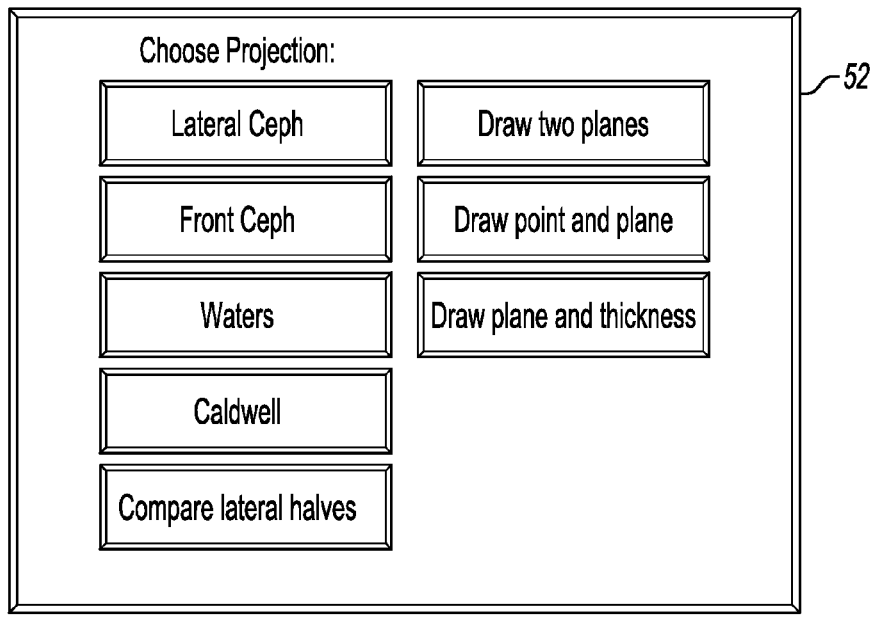
FIG. 2A illustrates a user interface for choosing among a plurality of synthetic projections.

Referring to FIG. 2A, a user interface may be provided for choosing among a plurality of synthetic views, before and/or after the CT scan is performed. For example, a user interface displays the available synthetic views to the user, e.g. buttons for each of "Ceph," "Waters," "Compare Halves," etc. For example, by clicking a button for "Ceph," a synthetic ceph scan is displayed. If the CT scan is performed after the user chooses which synthetic views may be desirable from the user interface, the CT scan can be optimized to provide sufficient information for each desired synthetic view, while minimizing x-ray dose. Alternatively, the CT scan can always be performed such that any of the available options for synthetic views will subsequently be available.

Figure 3:
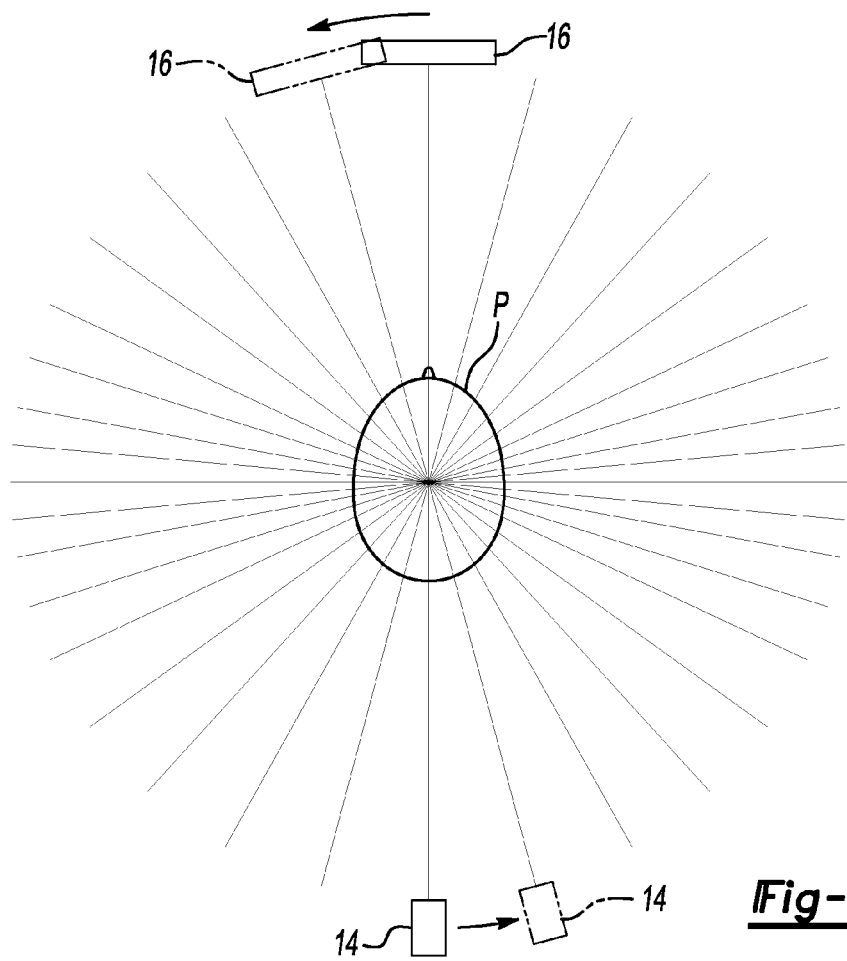
FIG. 3 illustrates one scanning technique that could be used to reduce dosage during the CT scan.

Because of the inherent noise reduction in the synthetic projection process, a very low dose CT scan is used. The CT scan itself would be considered to be well below what is considered diagnostic quality as a CT scan, but produces a synthetic projection that is very good diagnostic quality. Optional features of the present invention are provided to reduce x-ray dosage received by the patient even further. Referring to FIG. 3, during the rotation of the gantry 18 about the patient's head P, numerous x-ray images are taken at predetermined angular intervals and at predetermined dosages (i.e. the amount of time that the patient's head is exposed to the x-rays for each image) by the x-ray source 14 and detector 16. Although the intervals could all be equal through the rotation, and although the dosages could all be equal, the total dosage received by the patient can be reduced by increasing the angular intervals at some angular positions relative to the patient's head and/or by reducing the exposure dosage at some angular positions. Where the angles are increased and where the exposure is decreased may depend upon the type of projection to be synthesized. For example, for a lateral ceph scan, x-ray images from the front and rear of the patient's head can be at a lower dosage and can be taken and larger angular intervals than lateral x-ray images. The reconstruction software can account for the change in angular intervals and dosages in reconstructing the three-dimensional CT image. Less detailed information is needed at some angular positions than others. Note that the number of positions and the angular spacing shown in FIG. 3 is only for purposes of illustration. It is anticipated that more images would be taken than is shown, but fewer could be utilized.

Figure 4:
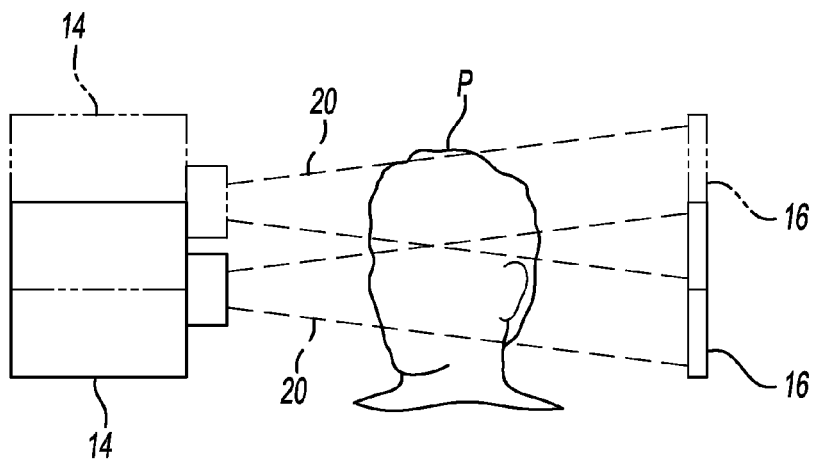
FIG. 4 illustrates an alternate method for using the scanning system of FIG. 1 to increase a vertical field of view.

Referring to FIG. 4, in order to increase the field of view of the resultant three-dimensional CT image, the CT scanner 12 may optionally be moved vertically during the scanning. Alternatively, a full scan can be performed of a lower section of the patient's head and a full scan can be performed of an upper section of the patient's head. The two full scans can be combined in the reconstruction algorithm to produce a single, continuous CT image. In either event, the angular intervals and/or dosages can be different for an upper section than for a lower section, depending upon where more resolution and contrast is desired (it is anticipated that more resolution and contrast would be desired in the lower section of a patient's head, including the jaw).

After the three-dimensional CT image is reconstructed (by on-board computer 40 and/or main computer 50), the CT image can be used to construct a selected or defined projection. The CT system 10 provides the user with several pre-defined projections and/or lets the user define their own projection, such as with the user interface shown in FIG. 2A. Generally, either by the pre-defined projections, or as custom-defined by the user, one way the projection can be generated is by defining an array of projection lines, e.g. between a point and a surface (a flat plane, curved plane, spherical, etc) or between two surfaces (parallel or not) and summing across the projection lines. The synthetic projections can mimic certain traditional views, such as the ceph scan, Water's view, Caldwell's projection, etc.

Figure 5A:
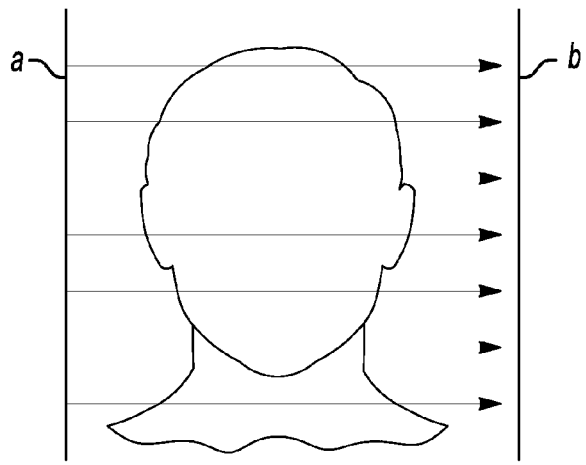
FIG. 5A illustrates the generation of a synthetic lateral ceph scan by a parallel projection based upon a CT image.
Figure 5B:
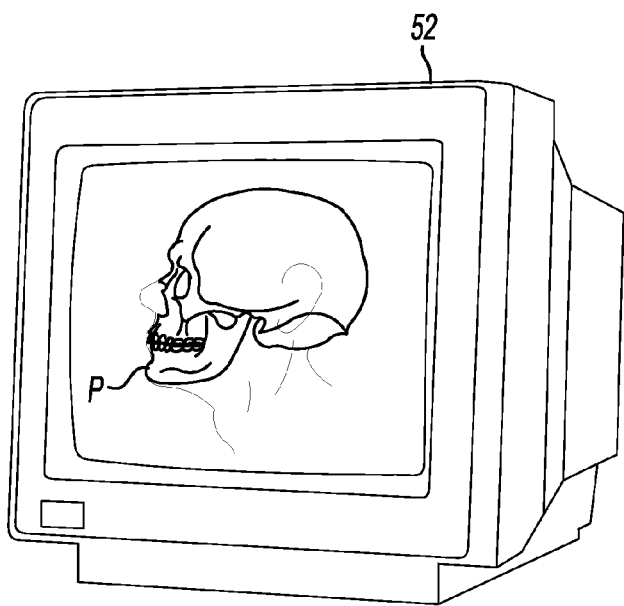
FIG. 5B illustrates a lateral ceph image generated by the scanning system of FIG. 1.

For example, referring to FIG. 5A, to simulate a lateral ceph scan, projection lines may be defined between two planes a and b, on either side of the patient's head P. Generally, by performing a forward projection based upon the three-dimensional CT image, a simulated or synthetic projection can be constructed. The synthetic lateral ceph scan projection is shown in FIG. 5B.

Figure 5C:
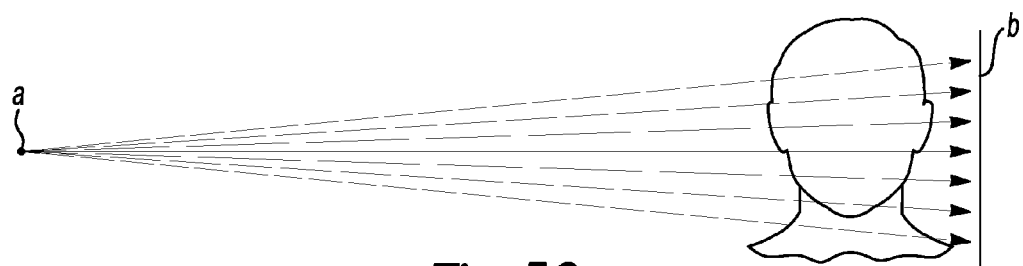
FIG. 5C illustrates the generation of a synthetic lateral ceph scan by projection lines that are substantially, but not completely, parallel.

The simulated projection can be constructed to simulate a projection under different circumstances. For example, referring to FIG. 5C, the simulated projection can be constructed to simulate a projection where the source is at a point a that is a certain distance from the patient's head P and the detector at a plane b. By choosing a source-to-patient distance of, for example, ten feet, prior ceph imaging systems can be simulated. A source (real or simulated) at ten feet does not provide a perfectly parallel projection, but may be advantageous because it provides a ceph image that is more similar to images to which the user (e.g. doctor or orthodontist) is accustomed. Optionally, the system 10 provides a user interface where the user can choose a simulated source distance between (for example) five ft to infinity (i.e. purely parallel projection).

Again referring to FIG. 5C, the point a and the plane b can be defined in a predefined synthetic projection that can be selected by the user via the user interface of FIG. 2A. Additionally, the user is also provided the option (via the user interface of FIG. 2A) of drawing a point a and a plane b anywhere relative to the three-dimensional image of the patient.

Another way of providing a synthesized image from a three-dimensional CT image is to view a slice that includes the patient's entire head P (or at least half of it). Generally, in viewing CT images, one can choose "slices" of the CT image to view at one time. In other words, the layers of tissue represented by the CT image are averaged across the chosen width of the selected slice and displayed. In order to display a ceph image (a lateral ceph image is shown for purposes of illustration in FIG. 5B), a width is chosen that is at least substantially equal (or even greater than) the width of the patient's head P. In this manner, all of the tissue of the patient's head P is averaged together, as would occur during an ideal parallel-projection ceph scan using the standard technique. The reconstruction algorithm to produce the three-dimensional CT image already removes any distortion caused by the incident angles of the x-rays from the x-ray source to the detector.

There are several advantages to using a CT scanner 12 to create a ceph image. First, a CT scanner 12 takes up substantially less room than a parallel projection ceph x-ray image device, since the source 14 and detector 16 can both be relatively close to the patient's head P. With a CT scanner 12, it is not necessary to place the source 14 a great distance from the patient's head P and the detector 16 in order to obtain a parallel projection. As explained above, the ceph image can provide either an ideal parallel projection ceph image or a simulated near-parallel projection that simulates current ceph projection systems.

Figure 6:
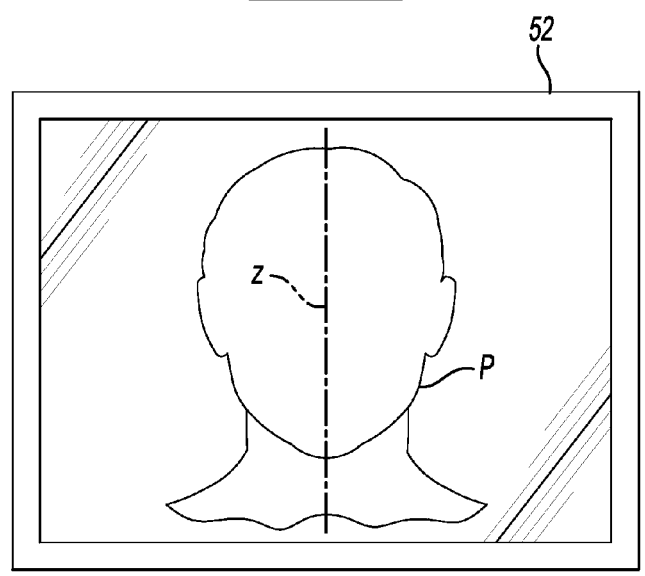
FIG. 6 illustrates a front ceph image generated by the scanning system of FIG. 1.

The CT image provides a great deal more other useful information that can be used in the ceph analysis or in the surgical, orthodontia or other planning. For example, a ceph image at any angle is readily available from the three-dimensional CT image, including a front ceph image, as shown in FIG. 6. This can be created in a manner similar to that used to create the lateral ceph image.

Other image manipulation can be performed with the CT image to assist in the ceph analysis that could not be done with a two-dimensional lateral ceph image. For example, referring to FIG. 6, the midplane z of the patient's head P can be determined manually or by the computer 50 (FIG. 1) based upon assumptions regarding symmetry of the patient's head P about the midplane z. The midplane z is useful in itself for many aspects of ceph analysis.

The synthetic projection can also provide a new view that is impossible or impractical with traditional x-ray equipment, such as a perfect parallel projection (FIG. 5A), or a projection that does not pass all the way through the patient. Two examples are described below, but many others would be useful.

Figure 7:
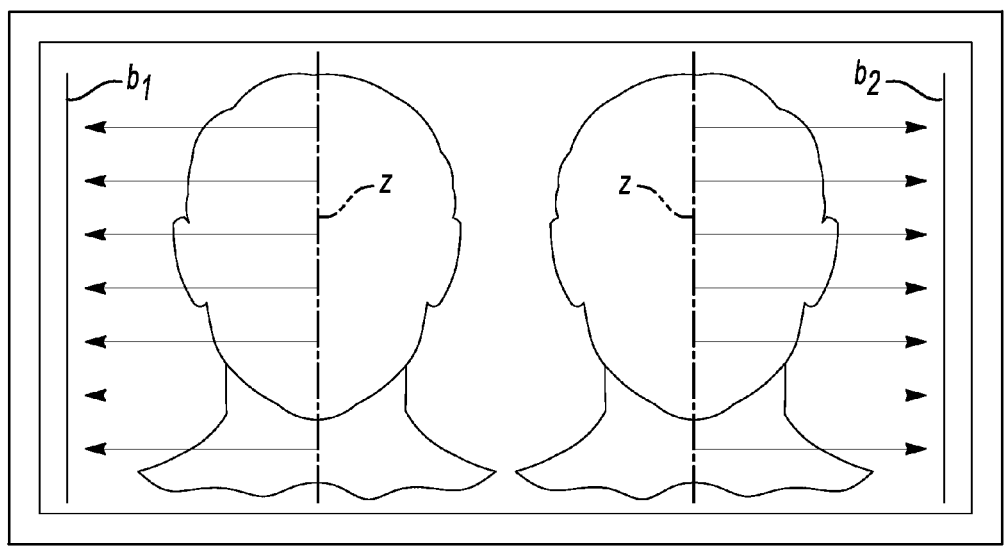
FIG. 7 illustrates the generation of two lateral half-ceph images.

Partial projections that span only half of the patient volume may be used to obtain "half-lateral" views as shown in FIG. 7. Projection lines are defined between the midplane z and a right plane $b_1$ and summed to create the right half lateral view. Projection lines are defined between the midplane z and a left plane $b_2$ and summed to create the right half lateral view. The left and right halves of the patient's head P can then be overlaid and displayed in different colors. That is, a left and right side lateral view that could be compared for symmetry, etc. This is impossible with traditional ceph imaging. Alternatively, one half could be inverted laterally to its mirror image (e.g. turning a left into a right half) and displayed in an overlapping relationship with the other, differently colored half. Areas where the two colors do not overlap clearly indicate a lack of symmetry. The overlapped halves can be displayed, rotated, enlarged and reduced in three-dimensional space on the display 52 selectively by the user input devices 54, 56. This option can be selected as the "compare lateral halves" option on the user interface of FIG. 2A.

An additional advantage with the CT image is that the "projection" can be re-oriented, manually or automatically, after acquisition to correct patient positioning errors. With a conventional x-ray (ceph, Water's view, panoramic, etc), a patient positioning error would require the x-ray to be redone or, more likely, the x-ray would be used with the positioning error, possibly leading to less accurate analysis. With the system 10, the projection lines are automatically properly oriented relative to the three-dimensional image of the patient (e.g. perpendicular to the midplane z for a lateral ceph scan).

Figure 8:
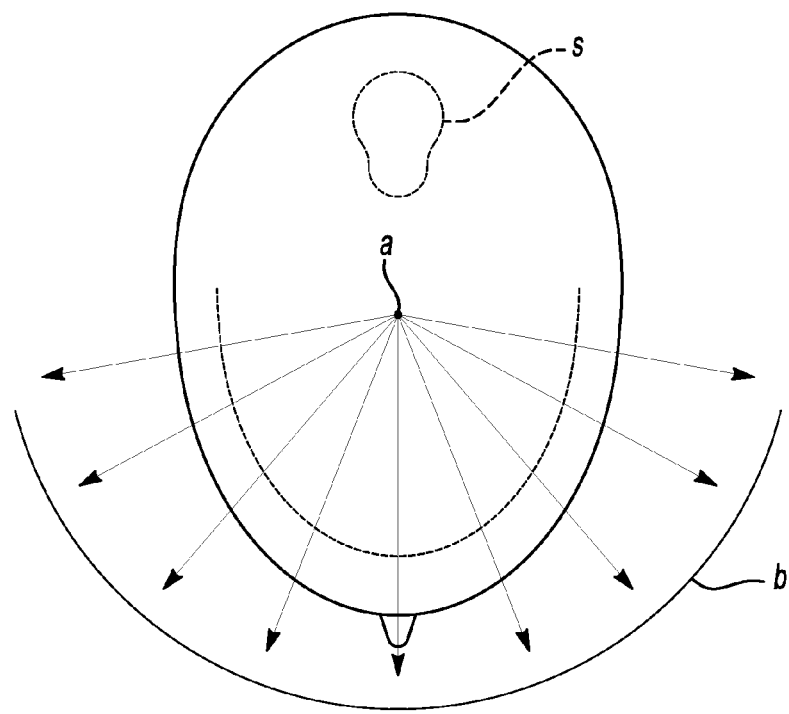
FIG. 8 illustrates the generation of a synthetic projection where the projection lines terminate within the patient.

The panoramic synthetic projection (selectable with the user interface of FIG. 2A) is illustrated in FIG. 8. Traditional panoramic x-ray imaging makes a projection image using x-rays that traverse the entire patient head. While the projections are optimized somewhat to minimize corruption of the image from non-jaw/non-mandible/etc. anatomy, such as the spine s and back of the skull, this corruption is inevitable. There will always be anatomical components outside of the true region of interest that corrupt a panoramic image. In a synthetically derived panoramic acquisition, this is not the case. One can project only over the region of interest. The synthetic panoramic view defines a point a within the patient P and a surface b around the front of the patient, as shown in FIG. 8. The synthetic projection is then created by summing the image along the projection lines between the point a and the surface b. This provides an image similar to the traditional panoramic view, but without corruption from the non-jaw/non-mandible anatomy. Alternatively, a surface can be defined inside the patient's head, rather than the point a.

With the CT system 10, the panoramic projection can be provided without any increase in x-ray exposure to the patient. For example, a current traditional panoramic x-ray machine typically exposes the patient to approximately 15 micro-Sieverts. A CT scan with a total exposure of 15 micro-Sieverts (with current technology) would produce a CT scan that is substantially below what would be considered "diagnostic quality." However, because of the noise reduction inherent in the synthetic projection generation, the CT scan does produce a very good diagnostic quality synthetic panoramic projection at 15 micro-Sieverts or less. It is anticipated that future advances in technology will further reduce the dosage required for a diagnostic quality CT scan, in which case the dosage required for the synthetic projections using the present invention will also decrease correspondingly.

Other options (selected via the user interface shown in FIG. 2A) permit the user to draw any point and any surface, or any two surfaces. The CT system then creates a synthetic view by summing the CT scan between the two custom drawn points/surfaces. Known drawing techniques can be used to position the point(s) and/or position and shape the surface(s).

Figure 9:
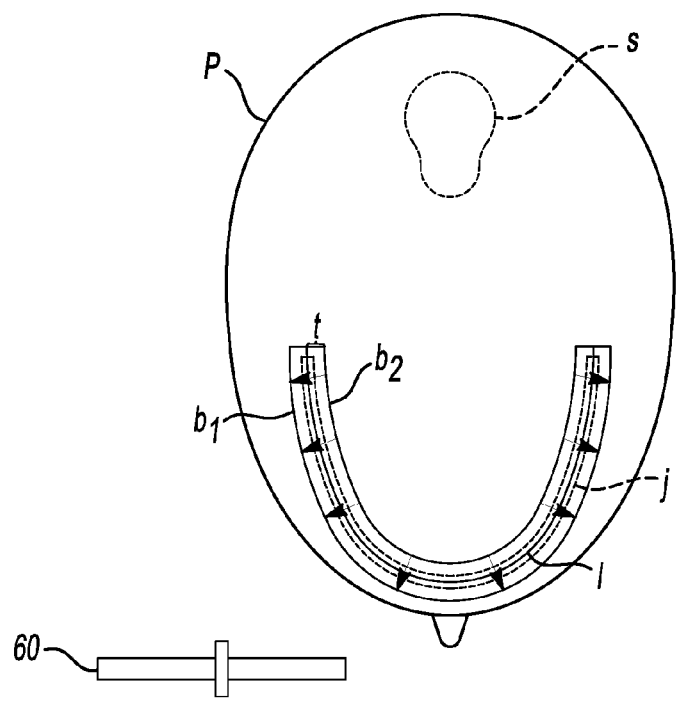
FIG. 9 illustrates one technique where a user defines a plane and thickness for a synthetic projection.

Another option (selected via the user interface shown in FIG. 2A) permits the user to draw a plane (flat or curved surface) on a two-dimensional section from the CT scan as shown in FIG. 9. A section taken through the jawline j of the patient's head P is shown in FIG. 9. Using the user interface, the user draws a line l, representing a surface normal to the section plane, and then selects a thickness (by entering a number or using a slider bar 60, etc). The thickness t is concurrently displayed over the section to define two surfaces $b_1$ and $b_2$, each spaced by the thickness t from the line l. The CT system 10 then creates a synthetic view based upon projection lines between and normal to the two surfaces $b_1$ and $b_2$. In the example shown, the user traced the jawline j of a patient on a horizontal section through the CT scan. The user can then chose a thickness t that encompassed the jaw. The CT system 10 then generated a "panoramic" view of just the jaw, without any artifacts from the rest of the head P.

The term "summing" as used herein is intended broadly to include any method of combining information across the projection line or lines. The invention is independent of the specific technique used to convert the information from the CT image to a defined projection.

In accordance with the provisions of the patent statutes and jurisprudence, exemplary configurations described above are considered to represent a preferred embodiment of the invention. However, it should be noted that the invention can be practiced otherwise than as specifically illustrated and described without departing from its spirit or scope. Alphanumeric labels on method steps are for ease of reference in dependent claims and unless otherwise specified do not require a specific sequence in which the steps are to be performed.

What is claimed is:

1. A method for generating an image of a patient including the steps of:

a) taking a plurality of x-rays of the patient;
    b) generating a three-dimensional image of the patient based upon the plurality of x-rays;
    c) generating a projection based upon the three-dimensional image of the patient and based upon a plurality of substantially parallel projection lines through a head of the patient;
    d) defining a lateral mid-line, which defines two lateral halves of the three-dimensional image of the head; and
    e) comparing the two lateral halves of the three-dimensional image of the head.

2. The method of claim 1 wherein said step e) further includes the step of inverting one of the two lateral halves.

3. The method of claim 2 wherein said step e) further includes the step of displaying the two lateral halves in different colors.

4. The method of claim 2 wherein said step e) further includes the step of aligning the inverted lateral half and the other of the two lateral halves.

* * * * *

UNITED STATES PATENT AND TRADEMARK OFFICE
CERTIFICATE OF CORRECTION

PATENT NO. : 7,397,890 B2  
APPLICATION NO. : 11/410526  
DATED : July 8, 2008  
INVENTOR(S) : Sukovic et al.

Page 1 of 1

It is certified that error appears in the above-identified patent and that said Letters Patent is hereby corrected as shown below:

Title page, line 5 insert the following after the title and before paragraph [0001] of the specification:

--STATEMENT REGARDING FEDERALLY SPONSORED RESEARCH OR DEVELOPMENT

This invention was made with government support under grant number R44CA107895, awarded by the National Institute of Health (NIH). The government has certain rights in the invention.--

Signed and Sealed this

Sixth Day of October, 2009

David J. Kappos  
*Director of the United States Patent and Trademark Office*